United States Patent [19]

White

[11] Patent Number: 5,108,383
[45] Date of Patent: Apr. 28, 1992

[54] MEMBRANES FOR ABSORBENT PACKETS

[75] Inventor: Lloyd S. White, Columbia, Md.

[73] Assignee: Allied-Signal Inc., Morris Twp., Morris Cty, N.J.

[21] Appl. No.: 447,722

[22] Filed: Dec. 8, 1989

[51] Int. Cl.$^5$ .............................................. A61F 13/15
[52] U.S. Cl. .................................................. 604/368
[58] Field of Search ............... 604/368, 358, 367, 369; 210/500.29, 500.3; 264/47, 241, 374

[56] References Cited

U.S. PATENT DOCUMENTS

| | | | |
|---|---|---|---|
| 3,133,137 | 5/1964 | Loeb et al. | 264/233 |
| 3,657,115 | 4/1972 | Manjikian et al. | 210/23 |
| 4,820,293 | 4/1989 | Kamme | 604/368 |

OTHER PUBLICATIONS

U.S. patent application Ser. No. 247,828, L. S. White, "Osmotic Absorbents", filed 9/22/88.

Primary Examiner—Randall L. Green
Assistant Examiner—R. Clarke
Attorney, Agent, or Firm—Harold N. Wells; Mary Jo Boldingh; Gerhard H. Fuchs

[57] ABSTRACT

An absorbent article comprising a cellulosic membrane about 5 to 50 μm thick prepared by casting a film from solution of a cellulose derivative in a suitable solution and these formed into a packet which encapsulates an osmotic promoter, particularly sodium chloride, sugar or other suitable compound, preferably having a molecular weight below about 500. The packet is capable of taking up at least 0.001 g/cm$^2$/min of water and retaining it against an external pressure of at least 0.689 kPa.

19 Claims, No Drawings

MEMBRANES FOR ABSORBENT PACKETS

PRIOR ART

This invention is related to absorbent articles which are used for many purposes, such as disposable diapers, absorbent pads, surgical dressings, and the like. Since most are intended to be disposable, the cost of the constituents is of great importance in combination with the performance.

Many disposable articles use wood fibers commonly known in the art as "wood fluff". Such fibers are inexpensive and have a large capacity for fluids but since the fluids are held between the fibers for the most part, they can be pressed out fairly easily. Also, since light wood fluff creates a relatively bulky product, more recently super absorbent polymer gels have been used in order to increase fluid capacity and decrease the bulk of the absorbent articles. Further discussion of conventional materials may be found in my related U.S. patent application Ser. No. 247,828 which is incorporated herein by reference. The present invention represents a significant improvement of the absorbent articles described there.

Another absorbent article is described by Kamme in U.S. Pat. No. 4,820,293. Osmotic pressure is said to assist in the absorptive process, but in relation to a very different objective and, consequently, the physical structure is quite different from the present invention. More particularly, Kamme was concerned with providing a surgical dressing which was to absorb blood and other fluids present at the site of a wound. Such fluids have constituents with relatively high molecular weight relative to water and consequently the semipermeable membrane employed is said to be of the dialysis type and the osmotic absorbent has a molecular weight above 500. Dialysis membranes are relatively open and are capable of preventing the passage of most useful blood components such as proteins, while passing lower molecular weight metabolic waste products, such as urea, through the membrane. Typically, dialysis is carried out under quite low differential pressures and relies on diffusion of the molecules through the porous membrane. In the Kamme absorbent article, the membrane is said to have pores in the range of 0.005–8 microns.

The absorbent packet of my previous application was shown to have the ability to pickup and retain large amounts of water relative to the weight of the membrane. However, it reached its maximum capacity only after an extended period and had a smaller uptake of liquid during the shorter typical period of use. Thus, a more rapid uptake of liquid has been sought to more nearly satisfy the needs of the market. The improved membranes to be discussed and the form in which they are used are directed toward those objectives.

SUMMARY OF THE INVENTION

Generally, the invention consists of an absorbent article capable of absorbing water and retaining said water against an external pressure which comprises:
(a) an osmotic promoter;
(b) a cellulosic membrane encapsulating said promoter having a thickness of about 5 to 50 μm produced by the process of
(1) casting a solution of a cellulose derivative and at least one liquid selected from the group consisting of acetone, dimethylformamide, dimethylacetamide, dimethylsulfoxide, 1-methyl-2-pyrrolidone, formamide, dioxane, tetraethylphosphate, acetic acid, tetrahydrofuran, and water, onto a suitable surface,
(2) removing the liquid from the film of (1),
(3) annealing the film of (2) in water,
(4) conditioning the annealed film of (3) in water containing a conditioning agent selected from the group consisting of glycerol, ethylene glycol, and propylene glycol,
(5) drying the conditioned film of (4).

The invention in a preferred embodiment is an absorbent packet which is capable of taking up at least 0.001 g/min/cm$^2$ of water and retaining said water against an external pressure of at least 0.1 psig (0.689 kPa) which comprises:
(a) An osmotic promoter;
(b) A cellulosic membrane encapsulating said promoter of (a) having a thickness of 5 to 50 μm, preferably less than 30 μm, and an hydraulic permeability of at least $$0.5 \times 10^{-5} \frac{cm^3}{cm^2\text{-atm-sec}},$$

and a salt permeability less than $$2.0 \times 10^{-7} \frac{g}{cm^2\text{-atm-sec}},$$

and produced by the process of
(1) casting a solution of a cellulose derivative, preferably cellulose acetate, more preferably cellulose diacetate, and at least one liquid selected from the group consisting of acetone, dimethylformamide, dimethylacetamide, dimethylsulfoxide, 1-methyl-2-pyrrolidone, formamide, dioxane, triethylphosphate, acetic acid, tetrahydrofuran, and water, onto a suitable surface,
(2) quenching the film of (1) in water at a temperature of 0° C. to 40° C.,
(3) annealing the quenched film of (2) in water at 75° C. to 95° C.,
(4) conditioning the annealed film of (3) in water containing a polyhydric compound selected from the group consisting of glycerol, ethylene glycol, and propylene glycol,
(5) drying said conditioned film.

If desired, steps (3) and (4) may be combined.

The quenching of (2) preferably will be carried out for 0.1 to 5 minutes using a water bath at 0° C. to 40° C. and usually following a brief period of air evaporation of the liquids.

The osmotic promoter may be chosen from various materials which provide a favorable osmotic pressure difference between the outside and the inside of the packet. Preferred are relatively low molecular weight compounds, preferably below 1000 molecular weight, such as sodium chloride, sugars, and other water soluble ionic salts, such as ammonium sulfate and calcium chloride. The amount of the osmotic promoter used is related to the amount of water to be taken up within the packet, the surface area of the packet, the desired rate of water uptake and the osmotic pressure which the compound is able to develop. Thus, less would be needed of a low molecular weight compound such as sodium chloride than of a higher molecular weight compound such as sugar. Broadly, the amount of promoter will be about 0.001 to 1 g per cm$^3$ of packet volume.

The packets may be fabricated in any form which is convenient for the intended end use. Individual packets can be made but preferably they will be produced as sheets in which the individual packets are defined by the sealing of two adjacent films in regular patterns, such as by heat or adhesives. An impermeable film also may be incorporated in the packets if desired.

DESCRIPTION OF THE PREFERRED EMBODIMENTS

Membranes

As discussed in my earlier application, osmotic membranes may be made from many materials. The membranes must pass large amounts of water and reject the osmotic promoter in order to maintain the pressure differentials. Ideally, the membrane should pass not only water but the salts and other compounds found in the bodily fluid which is to be absorbed. In practice, the ideal performance is only approximately achieved since the membrane which rejects the osmotic promoter usually will not easily pass the solutes found in body fluids. The membranes may be selected from those used as reverse osmosis membranes and may include cellulose acetate and derivatives thereof, polysulfone, polyelectrolyte complexes, long chain polyamides, interpenetrating polymer networks and interfacially formed reaction products as discussed in my patent application Ser. No. 247,828. For practical applications cost as well as performance must be considered and therefore for many applications cellulose acetate will be the material of choice for the osmotic membrane of the invention.

The methods for casting of cellulosic membranes are rather well known to those skilled in the art. An early example of such technique is found in Loeb et al. U.S. Pat. No. 3,133,137 which disclosed preparation of cellulose acetate membranes for desalination of water at relatively high pressure differentials. These membranes were cast from a solution using a solvent, water, and a pore-producing perchlorate salt. Subsequently, cellulose acetate membranes were cast from organic solutions including acetone and formamide, for example as in U.S. Pat. No. 3,657,115. The process which is used must be developed by experimentation and the properties of the finished membrane may or may not meet the particular requirements which are established for the selected end use. As noted above, the membranes used in experiments reported in my earlier application had capacity for large amounts of water but the rate at which the uptake occurred was not as rapid as would be desired for many applications. Clearly, in some applications the amount of fluid to be absorbed would be relatively uniform and small, while in others the amount would be large and intermittent. Thus, the membrane suitable for one application would not be useful in another application and one could not be certain that a membrane could meet the design criteria. It has been found that the method of preparing a cellulosic membrane can greatly affect its usefulness.

In general, a cellulosic membrane may be produced by casting a solution of a cellulose derivative, preferably cellulose acetate, more preferably cellulose diacetate, on a surface, such as glass or a plastic film, leveling the applied solution to produce a uniform film, and removing the solvent. The cast film is then conditioned, removed from the supporting surface and fabricated in the desired packet format.

Preferably, the cellulose derivative will be cellulose diacetate or triacetate or a mixture of the two, dissolved in at least one liquid selected from the group consisting of acetone, dimethylformamide, dimethylacetamide, dimethylsulfoxide, 1-methyl-2-pyrrolidone, formamide, dioxane, tetraethylphosphate, acetic acid, tetrahydrofuran, and water.

In a particularly preferred embodiment a solution of 15 to 25% cellulose diacetate dissolved in a suitable liquid mixture, such as acetone and formamide, is placed on a surface, particularly a plastic film, and leveled with a knife edge or its equivalent and then quenched in a water bath to solidify the membrane and to remove the solvent. Then the film is immersed in water at about 75° C. to 95° C. to anneal the film and then conditioned with an aqueous solution of a polyhydric compound such as glycerol, and thereafter dried in air. The cellulose acetate solution may contain in addition to acetone up to about 40% by weight of other liquids such as dimethylformamide, dimethylacetamide, dimethylsulfoxide, 1-methyl-2-pyrrolidone, formamide, dioxane, triethylphosphate, acetic acid, tetrahydrofuran, and water. The quenching of the film in water provides an asymmetric structure which promotes the desired osmotic properties. The water temperature is usually maintained in the range of about 0° C. to 40° C. Residence time in the water should be about 0.1 to 5 minutes. Following this quenching step the film has solidified and may be removed from the support or left on the support for the subsequent conditioning steps. The film is annealed at a temperature of 75° C. to 95° C. for a period of about 0.1 to 30 minutes. Then the film is conditioned by immersing it in water at a temperature of about 0° C. to 95° C. containing about 5 to 50 vol. % of glycerol or another suitable material such as ethylene glycol or propylene glycol. If desired, the annealing and conditioning steps may be combined.

The finished film may be characterized by having a thickness of about 5 to 50 microns, preferably less than 30 μm, an hydraulic permeability of at least $$0.5 \times 10^{-5} \frac{cm^3}{cm^2\text{-atm-sec}}.$$

and a salt permeability of less than $$2.0 \times 10^{-7} \frac{g}{cm^2\text{-atm-sec}}.$$

Permeability values can be determined by using an osmotic cell experiment as described by M. Matsuda and C. Kamizawa in *Desalination*, 49 (1984) 367-378.

$$J_v = L_p (\Delta P - \sigma \Delta \pi) \qquad \text{Equation 1}$$

$$J_s = \omega \Delta \pi + (1-\sigma) J_v C_s \qquad \text{Equation 2}$$

where:
$J_v$ = water flux
$J_s$ = solute flux
$L_p$ = hydraulic permeability
$\omega$ = salt permeability
$\Delta P$ = pressure difference across membrane
$\Delta \pi$ = osmotic pressure difference across membrane
$\sigma$ = reflection coefficient
$\bar{C}_s$ = mean solute concentration A reflection coefficient of 0.8 or greater is determined experimentally, which indicates that the film of the invention is operating as an osmotic membrane.

Preferably, the hydraulic permeability is greater than $1 \times 10^{-5}$ cm$^3$/cm$^2$-sec-atm and the salt permeability is less than $1 \times 10^{-7}$ g/cm$^2$-sec-atm. The ratio of water to salt permeabilities thus would be 100 or more.

Osmotic Promoter

Generally, the osmotic promoter will have a molecular weight below 1000, preferably below 500. In my earlier application I discussed potentially useful osmotic promoters, emphasizing the salts of Groups IA and IIA of the Periodic Table and particularly the halides of such metals. Sodium chloride is a particularly useful member of this group from both the standpoint of cost and performance. Other materials which may be used as osmotic promoters are sugars, polyhydric compounds such as ethylene glycol, ammonium compounds such as ammonium chloride, lactic acid, bicarbonates, and the like. The amount to be used will be fundamentally affected by the molecular weight of the promoter and its rejection by the membrane. Practically, the amount of the promoter will also be affected by the volume of the liquid to be absorbed by the packet since the promoter will be diluted by the water which passes through the membrane and the osmotic pressure differential will be reduced, which in turn reduces the flow of water through the membrane. On the other hand, if too much promoter is enclosed within the packet the water may continue to enter until substantial pressures are developed and the packet could be ruptured—an undesirable outcome if one wishes to retain the fluid within the packet. Thus the actual amount of the promoter which is used will depend upon the design parameters of the intended application, the size and strength of the packet, and the inherent ability of the promoter to develop an osmotic pressure differential. Broadly, the amount of promoter employed would be expected to be within the range of about 0.001 to 1 grams per cubic centimeter of the packet volume.

Packet Configuration

As I suggested in my earlier application, packets capable of picking up and retaining water or body fluids could be made in many forms. Generally, it is desirable that the packet be flexible since a stiff inflexible membrane would limit the packet's capacity and risk failure due to excessive pressure buildup. Thus, a flexible packet would be preferred in order to provide maximum capacity from the smallest initial volume. Any shape could be adopted which would be efficient in use and inexpensive to produce, although such requirements relate to practical application of the invention rather than to its effectiveness. The packets should be capable of withstanding an external pressure of at least 0.1 psig (0.689 kPa).

In one embodiment the packets would be formed from two sheets, one could be relatively impermeable and the other comprising a membrane of the invention or both could be such membranes. In the simplest form the two sheets could be joined at their edges as by gluing, heat sealing or the like. The two sheets would then become a single packet the size of the sheets. The packet could be included in a composite structure designed to pickup and retain fluids, which could include wood fluff or other absorbing materials, outer nonabsorbent sheets, fasteners and the like.

The membrane should be kept as thin as possible while retaining the needed strength. Thus, the preferred thickness is about 5 to 50 μm, preferably less than 30 μm. Casting the membrane on a temporary support avoids unnecessary weight since the support is later separated before the packets are assembled. The amount of water taken up by the packets relative to the weight of the membrane is very large, as the examples below illustrate—3000% or greater.

A more preferred embodiment is found in the division of the single packet described above into smaller packets by sealing the two sheets along interior lines, subdividing the two sheets into many smaller packets in a single unitary structure. Such a configuration has the advantage of avoiding a massive failure of the structure when filled with water since it is less likely that all of the sub-packets would fail at once. A desirable packet size has been found to be about 3 cm by 10 cm.

EXAMPLE 1

A solution of 22% cellulose diacetate (acetyl content: 39.4%, viscosity (ASTM-A): 44 sec.) with 33% formamide and 45% acetone was cast with a knife edge upon a polyethylene support film. After a 22 second evaporation time, the film was quenched in a 20° C. water bath. The membrane was removed from the support and annealed 15 minutes in 80° C. water, then immersed in 25 vol. % glycerol for about 30 minutes. The film was air dried to give a membrane with an average thickness of 25 microns, and then subjected to the following tests.

An osmotic cell was used to clamp a 20.27 cm$^2$ piece of membrane between a solution of water and 3% sodium chloride. With reference to equations 1 and 2 previously described, and using a reflection coefficient of 0.8, a hydraulic permeability of $1.30 \times 10^{-5}$ cm$^3$/(cm$^2$-sec-atm) and salt permeability of $2.00 \times 10^{-7}$ g/(cm$^2$-sec-atm) were determined.

As a practical test of the membrane of this invention a packet with surface area of 12.4 cm$^2$ was prepared by heat sealing after enclosing 0.110 grams of sodium chloride. To prepare the packet, a section of membrane was folded, then sealed along two edges to form an envelope where salt will be contained. Two edges of the envelope are formed by the heat seal, the third edge is the formed by the fold. The salt is placed within this envelope, and the fourth edge sealed. The packet was placed in 40 mL of stirred water and the weight gain and salt leakage from the packet was monitored. These results are listed in Table A. The average initial rate of the packet was 0.0225 g/min/cm$^2$.

TABLE A

| Sample No. | 1 |
|---|---|
| Membrane shell | 0.046 g |
| NaCl promoter | 0.110 g |
| Total weight | 0.156 g |
| Size (mm$^2$) | 20 × 31 |
| Area (cm$^2$) | 12.4 |

| Time (minutes) | Weight Gain (grams) | Wt. % salt in external solution |
|---|---|---|
| 0 | 0 | 0 |
| 5 | 1.392 | 0.0533 |
| 10 | 2.459 | 0.0950 |
| 15 | 3.174 | 0.1259 |
| 20 | 3.729 | 0.1512 |
| Uptake based on membrane weight | | 8107% |
| Initial average rate at T = 5 minutes | | 0.0225 g/min/cm$^2$ |

EXAMPLE 2

A solution of 22.5% cellulose diacetate (acetyl content: 39.4%, viscosity (ASTM-A): 44 seconds) with 30% formamide and 47.5% acetone was cast with a knife edge upon a polyester support film. After a 26 second evaporation time, the film was quenched in a 25° C. water bath. The membrane was removed from the support and annealed 10 minutes in 85° C. water, then immersed in 25 vol. % glycerol for about 30 minutes. The film was air dried to give membrane with an average thickness of 25 microns.

As in the previous Example, an osmotic cell was used to measure osmotic transport parameters for this membrane. Using a reflection coefficient of 0.95, a hydraulic permeability of $1.58 \times 10^{-5}$ cm$^3$/(cm$^2$-sec-atm) and salt permeability of $0.40 \times 10^{-7}$ g/(cm$^2$-sec-atm) were determined.

A test packet with surface area of 16.4 cm$^2$ was prepared by heat sealing as described above, wherein this packet contained 0.127 grams of sodium chloride. The packet was placed in 100 mL of stirred water and the weight gain and salt leakage from the packet was monitored. These results are listed in Table B. The average initial uptake rate of the packet for the first five minutes was 0.0246 g/min/cm$^2$.

This Example further illustrates how small changes in the process used to prepare the membrane allows control of the final properties. This test showed less salt leakage from the packet than observed in the previous Example, corresponding to the lower value for salt permeability. The transport ratio of water to salt, based on the permeability values determined with the osmotic cell, was 395.

TABLE B

| Sample No. | 2 |
|---|---|
| Membrane shell | 0.088 g |
| NaCl promoter | 0.127 g |
| Total weight | 0.215 g |
| Size (mm$^2$) | 21 × 39 |
| Area (cm$^2$) | 16.4 |

| Time (minutes) | Weight Gain (grams) | Wt. % salt in external solution |
|---|---|---|
| 0 | 0 | 0 |
| 5 | 2.015 | 0.0042 |
| 10 | 3.529 | 0.0078 |
| Uptake based on membrane weight | 4010% | |
| Initial average rate at T = 5 minutes | 0.0246 g/min/cm$^2$ | |

EXAMPLE 3

Membranes were prepared as before using a casting solution of 18 wt. % cellulose diacetate, 30 wt. % formamide, and 52 wt. % acetone, by casting upon a glass support plate. After 20 seconds the membrane was quenched in 20° C. water, delaminated, and then heated for 15 minutes in 80° C. water. The film was then soaked in an aqueous 30 wt. % glycerol solution for about 30 minutes, and then air dried. The resultant membrane thickness was 22 microns. The packets were formed with heat sealed edges as previously described and then tested against 10 mL of an unstirred synthetic urine solution containing 2 wt. % urea, 1 wt. % NaCl, 0.03 wt. % CaCl$_2$.2H$_2$O, and 0.06 wt. % MgCl$_2$.6H$_2$O. The results are given in Table C. The average initial rate was 0.0185 g/min/cm$^2$. At the end of 60 minutes, the packet had absorbed 38% of the available liquid. The percent increase in weight due to absorbed water is also calculated based on the weight of the membrane used to form the packet.

TABLE C

| Sample No. | 3 |
|---|---|
| Membrane shell | 0.046 g |
| NaCl promoter | 0.200 g |
| Total weight | 0.246 g |
| Size (mm$^2$) | 16 × 49 |
| Area (cm$^2$) | 15.7 |

| Time (minutes) | Weight Gain (grams) | Uptake based on Membrane Weight (%) |
|---|---|---|
| 0 | 0 | 0 |
| 5 | 1.448 | 3148 |
| 10 | 2.116 | 4600 |
| 15 | 2.663 | 5789 |
| 60 | 3.816 | 8296 |
| Initial average rate at T = 5 minutes | | 0.0185 g/min/cm$^2$ |

EXAMPLE 4

Membranes were prepared as before using a casting solution of 23 wt. % cellulose diacetate, 28 wt. % formamide, and 49 wt. % acetone, by casting upon a polyethylene support film. After 20 seconds the membrane was immersed in 20° C. water, delaminated, and then heated for 15 minutes in 80° C. water. The film was then soaked in aqueous 25 vol. % glycerol solution for about 30 minutes, and then air dried. The packets listed in Table D were formed with heat sealed edges, and then tested against 8 mL of the synthetic solution described in the previous Example 3. Packet 4 was prepared with sodium chloride as promoter, while Packet 5 used glucose. The packet with glucose as promoter has a slower initial rate than that with sodium chloride.

TABLE D

| Sample No. | 4 | 5 |
|---|---|---|
| Membrane shell | 0.038 g | 0.039 g |
| Promoter | NaCl | glucose |
| Promoter weight | 0.123 g | 0.103 g |
| Total Weight | 0.161 g | 0.142 g |
| Size (mm$^2$) | 18 × 28 | 18 × 28 |
| Area (cm$^2$) | 10.1 | 10.1 |

| Time (minutes) | Percent uptake based membrane weight | |
|---|---|---|
| 0 | 0 | 0 |
| 15 | 3384 | 1179 |
| 30 | 5013 | 2023 |
| 60 | 6960 | 3128 |
| Initial Average Rate at T = 15 (g/min/cm$^2$) | 0.0085 | 0.0030 |

EXAMPLE 5

Membranes were prepared as before using a casting solution of 22 wt. % cellulose diacetate, 20 wt. % 1-methyl-2-pyrrolidone, and 58 wt. % acetone, by casting upon a polyester support film. After 20 seconds the film was immersed in 25° C. water, delaminated, and then heated for 15 minutes in 80° C. water. The film was then soaked in 25 vol. % glycerol solution for about 30 minutes, and then air dried. The resultant film was 18 microns thick, and used to form the absorbent packets listed in Table E. These tests were against 100 mL of stirred water, and both the weight gain of the packet and salt content of the external solution were monitored.

TABLE E

| Sample No. | 6 |
|---|---|
| Membrane shell | 0.055 g |
| NaCl promoter | 0.101 g |
| Total weight | 0.156 g |

TABLE E-continued

| Size (mm²) | 20 × 37 |
|---|---|
| Area (cm²) | 14.8 |

| Time (minutes) | Weight Gain (grams) | Wt. % salt in external solution |
|---|---|---|
| 0 | 0 | 0 |
| 5 | 1.074 | 0.0022 |
| 10 | 1.914 | 0.0039 |
| 15 | 2.625 | 0.0052 |
| 20 | 3.167 | 0.0062 |
| 25 | 3.721 | 0.0072 |
| 30 | 4.369 | 0.0085 |
| Uptake based on membrane weight | 7944% | |
| Initial average rate at T = 5 minutes | 0.0145 g/min/cm² | |

EXAMPLE 6

Membranes were prepared as in Example 2, but with an evaporation time of 18 seconds. The resultant film had a thickness of 18 microns. This membrane was used to shape an absorbent packet that was tested against 100 mL of stirred water. The test listed in Table F was halted at 8 minutes, and 900 gram weight placed on top of the packet, whereupon no leaks were observed. If this weight is distributed over the total surface area of the membrane, then the packet withstood 1.1 psig (7.58 kPa gauge) without loss of absorbed water.

TABLE F

| Sample No. | 7 |
|---|---|
| Membrane shell | 0.044 g |
| NaCl promoter | 0.121 g |
| Total weight | 0.165 g |
| Size (mm²) | 16 × 37 |
| Area (cm²) | 11.8 |

| Time (minutes) | Weight Gain (grams) | Wt. % salt in external solution |
|---|---|---|
| 0 | 0 | 0 |
| 5 | 1.274 | 0.0030 |
| 8 | 1.960 | 0.0047 |
| Uptake based on membrane weight | 4455% | |
| Initial average rate at T = 5 minutes | 0.0215 g/min/cm² | |

EXAMPLE 7

Membranes were prepared with the process in Example 2. The resultant membrane had a thickness of 25 microns. A large packet was prepared as described above but with 5 internal compartments, each comprising about 1/5th the surface area and 1/5th of the sodium chloride content. The overall packet dimensions were 88 by 93 mm². The absorption was tested against 300 mL of stirred water. From Table G, an initial water absorption rate at 5 minutes of 0.0161 g/min/cm² was observed.

TABLE G

| Sample No. | 8 |
|---|---|
| Membrane shell | 0.559 g |
| NaCl promoter | 1.589 g |
| Total weight | 2.148 g |
| Size (mm²) | 88 × 93 |
| Area (cm²) | 164 |

| Time (minutes) | Weight Gain (grams) | Uptake based on Membrane Weight (%) |
|---|---|---|
| 0 | 0 | 0 |
| 5 | 13.182 | 2358 |
| 10 | 21.916 | 3921 |
| 15 | 25.411 | 4546 |
| 20 | 27.966 | 5003 |

TABLE G-continued

| Initial average rate at T = 5 minutes | 0.0161 g/min/cm² |
|---|---|

EXAMPLE 8

Membranes were prepared with the process in Example 2, but the hot water and glycerol treatment were combined into a single step of 3 minutes in 92° C. solution of 20 vol. % glycerol. The resultant membrane was 25 microns thick. A packet formed from this membrane was tested against 100 mL of stirred water, and the results are listed in Table H. An initial absorption rate of 0.0204 g/min/cm² was observed.

TABLE H

| Sample No. | 9 |
|---|---|
| Membrane shell | 0.054 g |
| NaCl promoter | 0.100 g |
| Total weight | 0.154 g |
| Size (mm²) | 16 × 42 |
| Area (cm²) | 13.4 |

| Time (minutes) | Weight Gain (grams) | Wt. % salt in external solution |
|---|---|---|
| 0 | 0 | 0 |
| 5 | 1.368 | 0.0015 |
| 10 | 2.425 | 0.0028 |
| Uptake based on membrane weight | 4491% | |
| Initial average rate at T = 5 minutes | 0.0204 g/min/cm² | |

I claim:

1. An absorbent article capable of absorbing water and retaining said water against an external pressure which comprises:
    (a) an osmotic promoter having a molecular weight below 1000;
    (b) a cellulosic membrane having reverse osmosis properties encapsulating said promoter having a thickness of about 5 to 50 μm produced by the process of
    (1) casting a solution of a soluble cellulose derivative in at least one liquid selected from the group consisting of acetone, dimethylformamide, dimethylacetamide, dimethylsulfoxide, 1-methyl-2-pyrrolidone, formamide, dioxane, tetraethylphosphate, acetic acid, tetrahydrofuran, and water, onto a suitable surface,
    (2) removing the liquid from the film of (1),
    (3) annealing the film of (2) in water,
    (4) conditioning the annealed film of (3) in water containing a conditioning agent selected from the group consisting of glycerol, ethylene glycol, and propylene glycol,
    (5) drying the conditioned film of (4).

2. The absorbent article of claim 1 wherein said osmotic promoter has a molecular weight below 500.

3. The absorbent article of claim 2 wherein said osmotic promoter is sodium chloride.

4. The absorbent article of claim 2 wherein said osmotic promoter is sugar.

5. The absorbent article of claim 1 wherein about 0.001 to 1 g of osmotic promoter is used for each cm³ of packet volume.

6. The absorbent article of claim 1 wherein a packet is formed from said membrane and the osmotic promoter encapsulated by closing said packet with heat sealing or adhesives.

7. The absorbent article of claim 1 wherein said membrane has a thickness less than 30 μm.

8. The absorbent article of claim 1 wherein said cellulosic membrane consists essentially of cellulose acetate.

9. The absorbent article of claim 8 wherein said cellulose acetate is cellulose diacetate.

10. The absorbent article of claim 9 wherein said liquid of (b) (1) is acetone and formamide.

11. The absorbent article of claim 9 wherein said liquid of (b) (1) is acetone and 1-methyl-2-pyrrolidone.

12. The absorbent article of claim 1 wherein said solution of (1) comprises 15 to 25 weight percent of cellulose acetate.

13. The absorbent article of claim 1 wherein the removal of the liquid (b) (1) comprises evaporating a portion of said liquid and thereafter quenching the resulting film in water at a temperature of 0° C. to 40° C.

14. The absorbent article of claim 1 wherein said article is capable of absorbing at least 0.001 g/cm$^2$/min of water.

15. The absorbent article of claim 1 wherein said external pressure is at least 0.689 kPa.

16. The absorbent article of claim 1 wherein said cellulosic membrane has an hydraulic permeability of at least $0.5 \times 10^{-5}$ cm$^3$/cm$^2$-atm-sec.

17. The absorbent article of claim 1 wherein said cellulosic membrane has a salt permeability of less than $2 \times 10^{-7}$ g/cm$^2$-atm-sec.

18. The absorbent article of claim 1 wherein said annealing of (b) (3) is carried out in water at a temperature of about 75° C. to 95° C.

19. The absorbent article of claim 1 wherein said conditioning of (b) (4) is carried out in water at a temperature of about 0° C. to 95° C. containing as a conditioning agent glycerol.

* * * * *